United States Patent
Richart

(10) Patent No.: US 10,383,695 B2
(45) Date of Patent: *Aug. 20, 2019

(54) PACKAGE FOR AN OBJECT AND AN ASSEMBLY INCLUDING SUCH A PACKAGE

(71) Applicant: DEPUY SYNTHES PRODUCTS, INC., Raynham, MA (US)

(72) Inventor: Oliver Richart, Lagord (FR)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/052,460

(22) Filed: Aug. 1, 2018

(65) Prior Publication Data

US 2018/0344423 A1    Dec. 6, 2018

Related U.S. Application Data

(60) Division of application No. 15/670,580, filed on Aug. 7, 2017, now Pat. No. 10,130,439, which is a
(Continued)

(30) Foreign Application Priority Data

Apr. 27, 2010 (FR) ...................... 10 53191

(51) Int. Cl.
   *A61B 50/30*     (2016.01)
   *B65B 69/00*     (2006.01)
   (Continued)

(52) U.S. Cl.
   CPC ............ *A61B 50/30* (2016.02); *A61B 17/865* (2013.01); *A61B 50/10* (2016.02); *A61C 8/0087* (2013.01);
   (Continued)

(58) Field of Classification Search
   CPC . A61B 17/865; A61B 17/8872; A61B 19/026; A61B 19/0256; A61B 50/10;
   (Continued)

(56) References Cited

U.S. PATENT DOCUMENTS 5,062,800 A    11/1991  Niznick
5,322,443 A *  6/1994   Beaty .................. A61C 8/0089
                                                 433/141
(Continued)

FOREIGN PATENT DOCUMENTS

DE    10146905    7/2003
WO    0002496     1/2000

OTHER PUBLICATIONS

International Search Report dated Oct. 19, 2011.

*Primary Examiner* — Luan K Bui
(74) *Attorney, Agent, or Firm* — Kramer Amado, P.C.

(57) ABSTRACT

A package for an object includes a support element with a coupler configured to hold the object captive in a given orientation of the object, and release the object by pivoting the object. The support element alone defines a first chamber containing the object, the support element also includes at least two parts that can be coupled and uncoupled relative to each other by inter-fitting with partial overlap, so as to form the first chamber containing the object. A stopper is coupled to the support element of the object by inter-fitting with partial overlap such that the support element presents a grip portion that projects from the stopper. A cover is coupled to the stopper by inter-fitting with partial overlap so as to cooperate with the stopper to define a second chamber inside which the grip portion of the support element extends, and while the cover is coupled to the stopper, a grip portion of the stopper projects from the cover.

14 Claims, 3 Drawing Sheets

Related U.S. Application Data continuation of application No. 14/997,630, filed on Jan. 18, 2016, now Pat. No. 9,750,579, which is a continuation of application No. 13/583,801, filed as application No. PCT/FR2011/050943 on Apr. 27, 2011, now Pat. No. 9,265,579.

(51) Int. Cl.
| | | |
|---|---|---|
| *A61B 50/10* | (2016.01) | |
| *A61B 17/86* | (2006.01) | |
| *A61C 8/00* | (2006.01) | |
| *A61C 19/02* | (2006.01) | |
| *A61B 17/88* | (2006.01) | |
| *A61B 50/00* | (2016.01) | |
| *A61B 50/20* | (2016.01) | |
| *A61L 2/20* | (2006.01) | |

(52) U.S. Cl.
CPC .............. *A61C 19/02* (2013.01); *B65B 69/00* (2013.01); *A61B 17/8872* (2013.01); *A61B 50/20* (2016.02); *A61B 2050/006* (2016.02); *A61B 2050/0054* (2016.02); *A61C 8/0089* (2013.01); *A61L 2/20* (2013.01); *A61L 2202/18* (2013.01); *A61L 2202/21* (2013.01)

(58) Field of Classification Search
CPC ............ A61B 50/30; A61B 2019/0206; A61B 2019/0213; A61C 19/02; B65D 77/26; B65B 69/00
USPC ....... 206/63.5, 363, 368, 369, 438; 433/167, 433/172–174; 53/492
See application file for complete search history.

(56) References Cited

U.S. PATENT DOCUMENTS

| | | |
|---|---|---|
| 5,437,550 A | 8/1995 | Beaty et al. |
| 5,538,428 A | 7/1996 | Staubli |
| 5,558,230 A | 9/1996 | Fisher et al. |
| 5,622,500 A | 4/1997 | Niznick et al. |
| 5,692,904 A | 12/1997 | Beaty et al. |
| 6,203,323 B1 | 3/2001 | Beaty et al. |
| 6,217,332 B1 | 4/2001 | Kumar |
| 6,247,932 B1 | 6/2001 | Sutter |
| 6,287,117 B1 | 9/2001 | Niznick |
| 7,854,316 B2 | 12/2010 | Park et al. |
| 7,921,991 B2 | 4/2011 | Sato et al. |
| 8,083,054 B2 * | 12/2011 | Nihei .................. A61C 8/0087 206/368 |
| 2003/0221977 A1 | 12/2003 | Kumar et al. |
| 2005/0098460 A1 | 5/2005 | Smith et al. |

\* cited by examiner

PACKAGE FOR AN OBJECT AND AN ASSEMBLY INCLUDING SUCH A PACKAGE

RELATED APPLICATION

This application is a divisional application of allowed U.S. patent application Ser. No. 15/670,580, filed on Aug. 7, 2017, which in turn is a continuation of U.S. patent application Ser. No. 14/997,630, filed on Jan. 18, 2016 (now U.S. Pat. No. 9,750,579), which is a continuation of U.S. patent application Ser. No. 13/583,801, filed on Sep. 10, 2012 (now U.S. Pat. No. 9,265,579), which is a National Phase of PCT/FR2011/050943, filed on Apr. 22, 2011 which claims priority to FR 10 53191 filed on Apr. 27, 2010, the entirety of which are incorporated by reference.

BACKGROUND

Field of the Invention

The present invention generally relates to packages for objects, in particular for medical components that are preferably sterilized.

Description of Related Art

In the prior art, packages are known that are in the form of plastic blister shells or bags in which an object is contained. For medical components that must be unpackaged in near-aseptic conditions, such packages pose problems of contamination while the package is being passed from one person to another and while said package is being opened. Specifically, from its departure from a "dirty" work zone, i.e. without special aseptic conditions, to its arrival in a "clean" work zone, i.e. a work zone in which given aseptic conditions are maintained, e.g. the zone of an operating block, the package that arrives in the clean zone is contaminated on the outside, and this presents a risk of the medical object being contaminated while it is being removed from said package.

In order to limit the risk of contamination, it is known to open the bag in such a manner as to cause the object to fall onto a worktop without any need to touch said object. Only a sterile assistant or surgeon picks up the object. However, a solid object runs the risk not only of being damaged on impact with the worktop, or even of rolling onto the floor, but also of being contaminated by foreign bodies present on the worktop.

Document U.S. Pat. No. 5,062,800 describes a medical package for a dental implant that includes a support element provided with fastener means for fastening the implant, and a stopper that can be coupled to the support element in such a manner that the support element projects from said stopper. Said package also includes a cover that covers the stopper. However, the cover completely covers the length of the stopper such that the operator has no option other than to empty the content of the cover by causing said content to fall onto a worktop. As mentioned above, causing the implant to fall may damage it and increases the risk of contamination.

OBJECTS AND SUMMARY

An object of the present invention is to propose a package for packaging and unpackaging an object, which package makes it possible to limit the risks of contamination of the object, while making it possible to unpackage the object without having to let get of it or touch it directly.

To this end, the invention provides a package for an object such as a preferably-sterilized medical component, said package being characterized in that it comprises:
  a support element provided with means for coupling said object to said support element;
  a first hollow protective element, referred to as a stopper, that can be coupled to the support element of said object, preferably by interfitting with partial overlap, such that the support element presents a portion, referred to as a "grip portion", that projects from said stopper;
  said support element, alone or in co-operation with the stopper, defining a first chamber containing said object; and
  a second hollow protective element, referred to as a cover;
  said package being further characterized in that said cover can be coupled to the stopper, preferably by interfitting with partial overlap, so as to co-operate with said stopper to define a second chamber inside which said grip portion of the support element extends; and
  in that, while the cover is coupled to the stopper, a portion, referred to as a "grip portion", of the stopper projects from the cover.

By means of the grip portions of each of the protective elements and of the support element, which support element projects from the protective element to which it is coupled, the chambers defined by interfitting said elements, with partial overlap, can be opened until the object can be accessed, without ever letting go of or touching said object, and with a reduced risk of the object being contaminated.

Specifically, while the package is being passed from a first operator to a second operator, the protective cover may be removed in such a manner as to open the first chamber so as to uncover the grip end of the support element of the object and retain, for the second operator, only the sub-assembly formed of the stopper and of the support element.

Since the second operator holds said sub-assembly by the end of the stopper remote from the support element, the end of the support element uncovered by opening the first chamber is clean and may be offered to the last operator, e.g. the surgeon. The last operator is the operator who takes hold of the object by means of an instrument in order to use it.

Naturally, the first operator and the second operator may be a single operator who removes the cover from the stopper by taking hold of the cover with one hand and the stopper with the other, so as to uncover the support element.

The stopper and the support element may thus be separated in such a manner as to open the chamber containing the object that remains coupled to the support element held by the last operator. The last operator who thus retains only the support element to which the object is coupled can use the clean hand that holds the grip end of the support element to deactivate the coupler means, and can use the other hand, which is also clean, to take hold of the object, e.g. by means of an instrument.

Such a design of the package of the invention makes it possible to make a package with a small number of parts, mainly three, so that while the package is being passed from a dirty zone to a clean zone via various people, neither the support element nor the object are touched by a person in the dirty zone, and the object coupled to the support element is never let go. The risk of contamination is thus very greatly reduced.

According to an advantageous characteristic of the invention, the stopper and the cover are each formed by a respective elongate hollow body that is open at one end and closed at the other end.

The elongate nature of the object-protecting elements formed by the cover and the stopper, makes it possible to benefit from a safety distance while the chambers are being opened and the various portions of the package are being passed from one person to another. Specifically, two people may take hold of the outside of the package formed by the stopper and the cover, or of the sub-assembly of the package formed by the stopper and the support element, each holding a respective opposite end, thereby reducing the risk of contamination.

According to an advantageous characteristic of the invention, the means for coupling the object to the support element comprise a deformable body, referred to as a valve, presenting an orifice, preferably of oval shape, that is capable of passing, by deformation of said body, from a "retaining" configuration in which said orifice of the valve presents a shape and/or dimensions making it possible to clamp the object, to a "releasing" configuration in which said orifice presents a shape and/or dimensions making it possible to release said object relative to said orifice of the valve.

In another particular embodiment of the coupler means, of the type for which said object presents an elongate body, said means for coupling the object to the support element include a deformable elongate body, referred to as a mandrel, along and inside which an orifice is formed for inserting the object. Said means also include a bellows that surrounds the mandrel and that is capable of passing from a deployed position of the folds of the bellows, in which said bellows bears against the mandrel in such a manner as to clamp the insertion orifice around the object, to a compressed position of said folds of the bellows, in which the bellows does not press against the mandrel so as to enable the object to move relative to said insertion orifice for inserting the mandrel.

Preferably, said support element includes at least two arms that are spaced apart from each other and that extend on either side and along the assembly formed of the mandrel and of the bellows.

In another particular embodiment of the coupler means, the means for coupling the object to the support element present a configuration for holding the object captive in a given orientation of said object, and a configuration for releasing said object by pivoting it.

In another particular embodiment of the coupler means, the support element and the means for coupling the object to the support element are configured to hold the object suspended through said coupler means, in such a manner as to make it possible to see the length of said object while said object is coupled to the support element.

According to an advantageous characteristic of the invention, said support and protective elements of the package are interfitted, with partial overlap, by friction and/or by screw-fastening.

In a particular embodiment of said package for which said support element alone defines said first chamber containing said object, and said support element is formed of at least two parts that can be coupled and uncoupled relative to each other, preferably by interfitting with partial overlap, so as to form said first chamber containing said object.

In another particular embodiment of said package for which said support element co-operates with the stopper to define said first chamber containing said object, said support element defines an open cavity that is to be closed by the stopper.

Preferably, said stopper, and possibly the cover, present(s) at least one predefined location for positioning at least one finger of a person.

Advantageously, the support element and/or the stopper and/or the cover present(s) a portion, preferably formed by a membrane, that is impermeable to bacteria but permeable to gas so as to enable said first chamber and/or said second chamber to be sterilized with gas.

The invention also relates to a method of unpackaging a preferably-sterilized medical object contained in a package as described above, said method being characterized in that it comprises the following steps:
  a) a first person separating the cover from the stopper in such a manner as to uncover the support element;
  b) a second person distinct from said first person taking hold of the support element; and
  c) separating said support element from the stopper while the stopper is being held by the first person.

Naturally, provision may be made for the cover and the stopper to be separated by two different people in a dirty zone, instead of by a single person, with one holding one end of the stopper and the other holding one end of the cover.

Advantageously, said method comprises the following additional steps:
  d) optionally putting said support element that closes the object on standby in a standby zone, while said object is waiting to be used; and
  e) opening the first chamber defined by said support element in order to remove said object.

The invention also relates to an assembly comprising an object such as a preferably-sterilized medical component and a package as described above containing said object coupled to said support element.

Preferably, said object presents an end for gripping, e.g. by an instrument, said object being coupled to the support element in such a manner that its grip end is free and points away from the grip portion of the support element.

BRIEF DESCRIPTION OF THE DRAWINGS

The invention can be well understood on reading the following description of embodiments, with reference to the accompanying drawings, in which.

DETAILED DESCRIPTION

Figure 2:
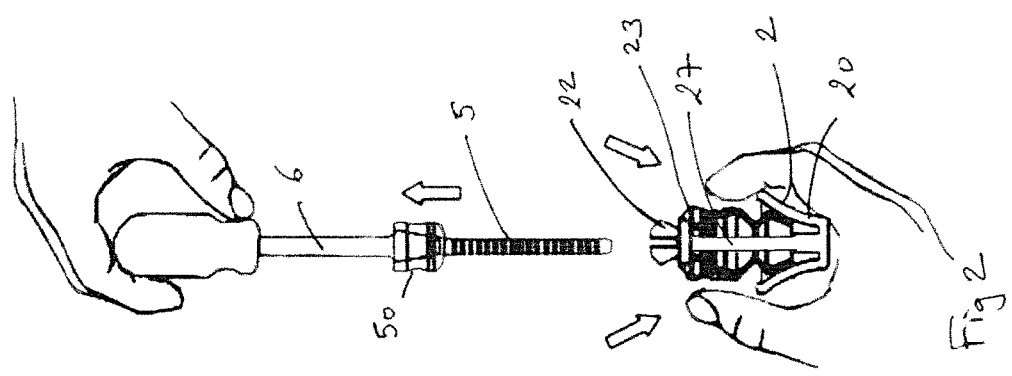
FIG. 2 is a section view of the support element in a second embodiment of the package in which the coupler means for coupling the medical component to the support element are formed by a mandrel surrounded by a bellows.
Figure 1:
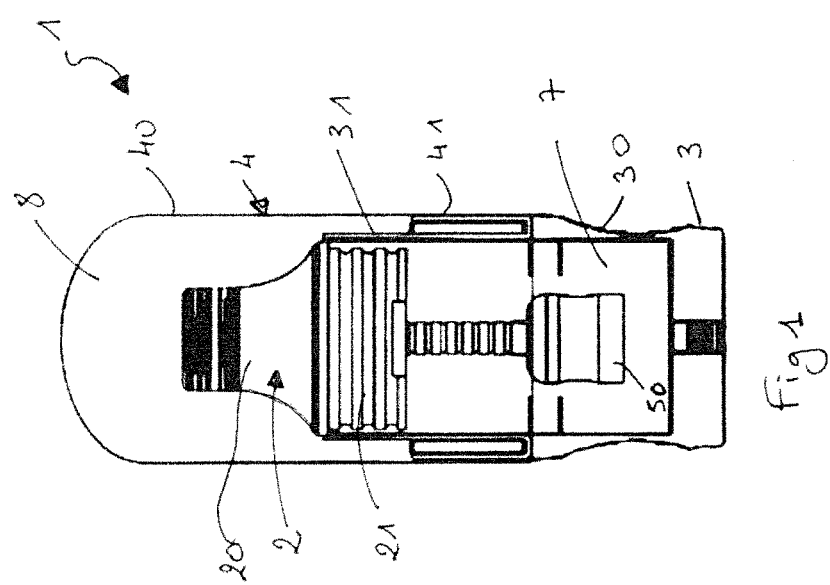
FIG. 1 is a view of a package of the invention in accordance with a first embodiment, inside which a medical component is packaged.
Figure 1C:
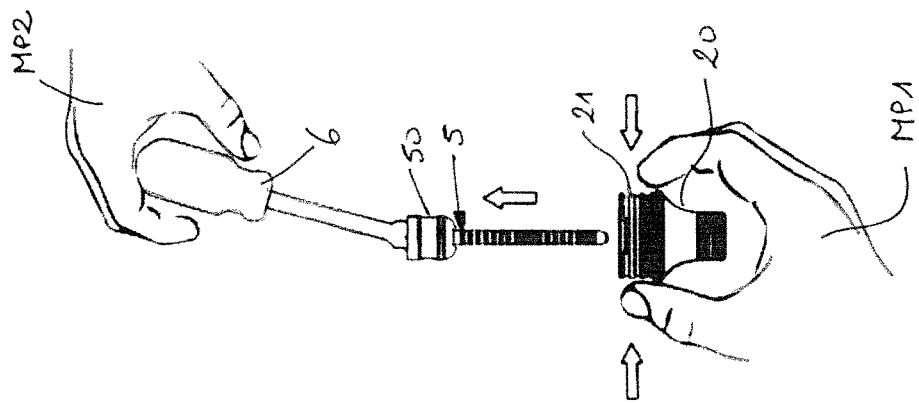
FIG. 1C is a view of the support element of the FIG. 1B package during a third step of unpackaging in which the third operator, who is holding the support element in one hand, uses the other hand to take hold of the medical component by means of a tool, so as to remove it from the support element, while deactivating the coupler means for coupling the medical component to the support element.
Figure 1B:
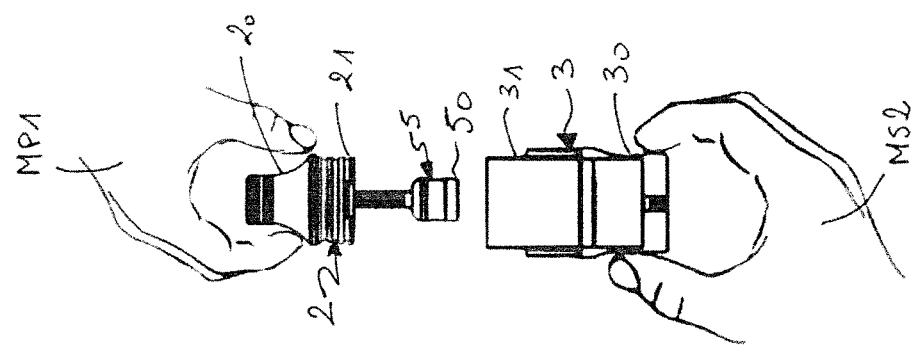
FIG. 1B is a view of the sub-assembly of the FIG. 1A package during a second step of unpackaging in which the stopper is removed, remaining in the hand of the second operator in the "dirty" zone, and the component support is held at its end remote from the medical component by the hand of a third operator in a clean zone.
Figure 1A:
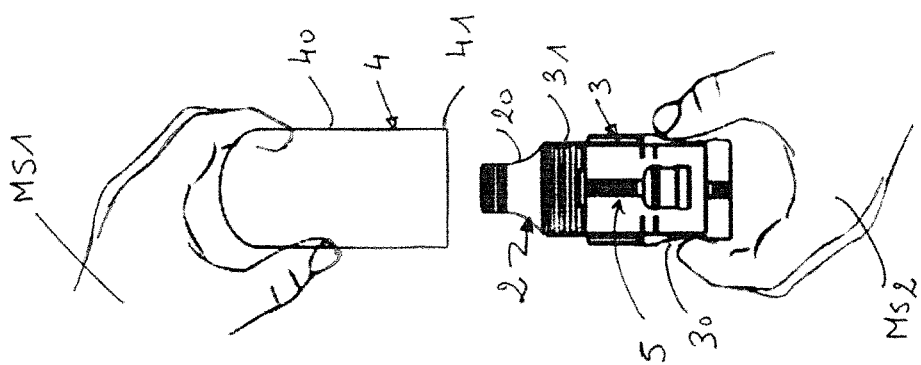
FIG. 1A is a view of the FIG. 1 package during a first step of unpackaging in which the cover is removed, remaining in the hand of a first operator in a "dirty" zone, and the remaining sub-assembly formed of the stopper and of the component support is held at its stopper end by the hand of a second operator in the "dirty" zone.

The term "dirty" or "contaminated" is used of a person working in non-acepticized conditions, who might contaminate, by hand, any object touched. Conversely, the term "clean" is used of a person working in conditions that are sufficiently aseptic.

With reference to the figures and as mentioned above, the invention provides a package 1 for an object, such as a medical component, for the purpose of preserving the sterile nature of the object, and in order to enable the object to be unpackaged in aseptic or near-aseptic conditions. In the embodiment shown in the figures, said object is a screw for surgery of the cervical spine or a screw for surgery of the lumbar spine, but the invention also applies to other types of object, in particular to other types of implant.

Said package includes a support element 2 provided with means 21; 22, 23; 24, 25; 26 for coupling said object 5 to said support element 2, and a first hollow protective element 3, referred to as a stopper, that can be coupled to the support element 2 of said object 5, by interfitting with partial overlap.

While the stopper 3 is coupled to the support element 2, said support element 2 and the stopper 3 define between them a first chamber 7 containing said object 5. Furthermore, the stopper 3 covers the support element 2 in part, such that the free end portion 20, referred to as the "grip end", of the support element 2 projects from said stopper 3 so that said free end portion 20 forms a grip zone.

When it is stated that the support element 2 is provided with means for coupling said object 5 to said support element 2, the term "coupling" means that said object cannot come apart from said support element without taking a specific action. Provision may be made for said object to be coupled to the support element by a narrow passage inside said first chamber, in such a manner as to prevent said object from escaping from said support element. Advantageously, provision may be made for said coupler means to also include breakable means making it possible to release the object from the support element.

Said package also includes a second hollow protective element 4, referred to as a cover, that can be coupled to the stopper 3 by interfitting with partial overlap, coming to cover the end 31 of said stopper 3, which itself covers the support element 2 of the object 5. The stopper 3 and the cover 4 are interfitted with partial overlap in such a manner as to define a second chamber 8 inside which the grip portion 20 of the support element 2 extends, and such that the end 30 of the stopper 3, remote from its end 31 of stopper 3 that covers the support element 2, projects from the cover 4 such that said free end portion 30 of the stopper 3 forms a grip zone. The end 40 of the cover 4, remote from the stopper 3, also forms a grip portion of the package, remote from the end 30 of the stopper.

Thus, each element of the package, namely the support element 2, the stopper 3, and the cover 4, presents a grip end 20, 30, 40 remote from its opposite end that is interfitted with another element of the package. Said elements are interfitted in such a manner as to define a chamber 7, 8 between two interfitted elements, preferably a chamber that is sealed at least against bacteria. Thus, the interfitted elements of the package define two chambers 7, 8 of which one 7 is defined between the stopper and the cover, inside which the object is housed, and which can only be accessed once open, the other chamber 8 serving to protect the grip end 20 of the support element 2.

Such a design of the package makes it possible to handle it without any risk of contaminating the object contained in the presentation chamber and without having to let go of said object.

Specifically, the package held by the end 40 of the cover 4 by a first person in a dirty zone may be offered to a second person, also in a dirty zone, who takes hold of the opposite end 30 of the package formed by the free end of the stopper 3. The second person pulls on the stopper 3 in such a manner that the cover 4 remains in the hand of the first person, and this makes it possible to uncover a clean grip zone 20 of the support element 2, remote from the end 30 held by the second person. Specifically, the clean grip zone 20 of the support element 2 was previously housed in the chamber 7 defined between the cover 4 and the stopper 3. Then, said second person offers the remaining sub-package to a third person in a clean zone, who thus takes hold of the clean end 20 of the support element 2 that projects from the stopper 3. As above, the third person pulls on the support element 2 in such a manner as to keep hold only of said support element 2 and the object coupled to said support element. With the other hand, and by means of an appropriate instrument, the same operator removes the object from its support element 2 as described below. In a variant, the first person and the second person may be the same person.

Preferably, the stopper 3 and the cover 4 are each formed by a respective elongate hollow body that is open at one end and closed at the other end, i.e. a tube closed at one end. The design of each of the protective elements in the form of an elongate body like a test tube makes it possible to benefit from a safety distance between the grip end 40 of the cover 4 and the grip end 30 of the stopper 3.

Such a distance between the grip ends 30, 40 of the package makes it possible to limit the risk of contamination at the grip end 20 of the support element 2 that extends in the chamber 8, when said chamber 8 is opened by separating the cover 4 and the stopper 3. In addition, the distance between the grip end 30 of the stopper 3 and the grip end 20 of the support element 2 makes it possible to limit the risk of contamination while the support element 2 is being passed to a sterile "clean" operator, who can thus take hold of the support element by its free end 20 at a distance from the potentially-contaminated end 30 of the stopper.

In the embodiment shown in FIGS. 1, 1A, 1B, 1C, the means 21 for coupling the object to the support element comprise a deformable body 21, referred to as a valve, presenting an orifice, preferably of oval shape, that is capable of passing, by sideways deformation of said body relative to the axis of said orifice, from a "retaining" configuration in which said orifice of the valve 21 presents a shape and/or dimensions making it possible to clamp the object 5, to a "releasing" configuration in which said orifice presents a shape and/or dimensions making it possible to release said object 5 relative to said orifice of the valve 21.

In the relaxed state, the orifice of the valve 21 is naturally in the retaining position. Thus, for an orifice of shape that is oval or elliptical in its natural state, i.e. when relaxed, deforming said orifice by pressing sideways on the opposite ends of the ellipse or the oval, deforms the oval or elliptical orifice into a substantially-circular orifice of diameter that is greater than the minor diameter of the ellipse or oval, and this makes it possible to release the object that is no longer pressed against the wall of the orifice. Naturally, the orifice of the valve is dimensioned so that in its non-deformed state, its minor diameter is less than the diameter of the object, but in its deformed state, its minor diameter is greater than said diameter of the object.

In another embodiment of the coupler means shown in FIG. 2, that finds an advantageous application for an object presenting an elongate body, said means 22, 23 for coupling the object to the support element include a deformable elongate body 22, referred to as a mandrel, along and inside which an orifice is formed for inserting the object.

Said means 22, 23 also include a bellows 23 that is threaded on the mandrel 22 and that is capable of passing from a deployed position of the folds of the bellows, in which said bellows bears against the mandrel 22 in such a manner as to clamp the insertion orifice around the object 5, to a compressed position of said folds of the bellows, in which the bellows does not press against the mandrel 22 so that the orifice is unclamped and the object is free to move relative to the orifice.

When the mandrel is relaxed, the orifice of the mandrel 22 is dimensioned to present an opening that is large enough to receive the elongate body of the object, without damaging or rubbing against the mandrel.

In the deployed configuration of the bellows along the mandrel, i.e. in the free configuration of the folds of the bellows, said bellows bears via its top portion against the top portion of the mandrel, such that the inner wall of the orifice of the mandrel clamps on the body of the object, at the opening for inserting the body in the mandrel.

In order to couple the object to the assembly formed of the mandrel and of the bellows, the bellows is compressed so as to relax the orifice of the mandrel in order to make it possible to insert the body of the object into said orifice, then the bellows is released so that it bears against the mandrel in such a manner as to clamp the orifice around the body of said mandrel. The object is released by compressing the bellows so that the orifice is no longer pressed around the object, and so as to make it possible to remove it by means of an instrument.

Preferably, as shown in FIG. 2, said support element 2 also includes at least two arms 27 that are spaced apart from each other and that extend on either side and along the assembly formed of the mandrel 22 and of the bellows 23.

Said arms project from the support-element portion that is provided with coupler means for coupling the object and they extend along the axis for interfitting said support element with the stopper, in such a manner as to co-operate with the wall of the stopper for interfitting the stopper and the support element, with partial overlap.

In particular, the stopper 3 covers the arms 27 in such a manner that the arms make it possible to guide and stiffen the stopper and support-element assembly while protecting the bellows 23 relative to the stopper 3 so that said bellows are not deformed while the stopper is being closed or opened relative to the support element.

The space between the arms enables the operator to access the bellows so as to compress it in order to insert or release the object held in the orifice of the mandrel.

Figure 4:
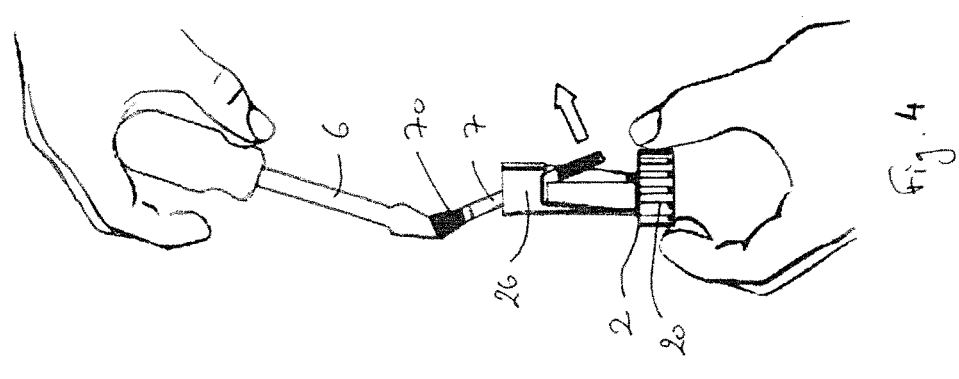
FIG. 4 is a section view of the support element in a fourth embodiment of the package in which the coupler means for coupling the medical component to the support element are formed by an element presenting a housing that is suitable for holding the component in a given orientation and for enabling it to be released by turning or tilting, thereby disengaging said component sideways.

In another embodiment of the invention shown in FIG. 4, the means 26 for coupling the object to the support element present a configuration for holding the object captive in a given orientation of said object, and a configuration for releasing said object by pivoting it. Provision may be made for the coupler means 26 to include a housing in which the object is held by resilient clamping or by snap-fastening. In the embodiment shown in FIG. 4, the object is a cervical screw 7 having a head 70 that is suitable for co-operating with the instrument 6 so as to enable the operator to pivot the body of the screw 7 in order to release it from the coupler means 26. In particular, the object is released by pivoting it about an axis that is orthogonal to the axis of the housing and that corresponds to the longitudinal axis of the object.

Figure 3:
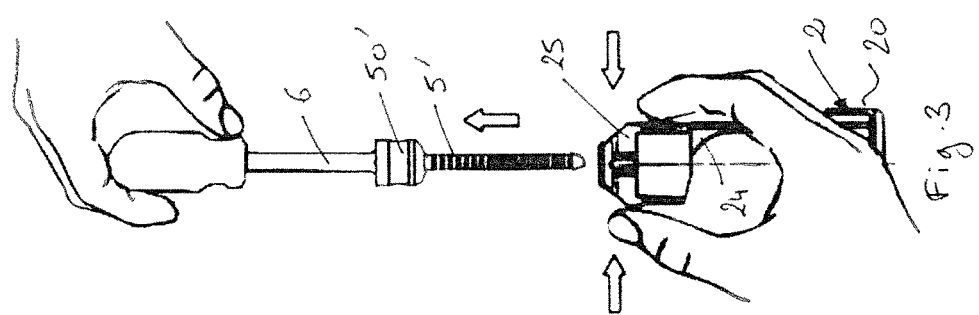
FIG. 3 is a section view of the support element in a third embodiment of the package in which the coupler means for coupling the medical component to the support element are formed by a valve-type deformable element having an orifice that is configured so as to clamp onto the medical component that passes therethrough, thereby coupling it to the support element, and so as to release said component when said valve is deformed.

In particular embodiments of the invention shown in FIGS. 3 and 4, the support element 2 and the means 24, 25; 26 for coupling the object to the support element are configured to hold the object suspended through said coupler means, in such a manner as to make it possible to see the length of said object while said object is coupled to the support element 2.

To this end, the support element comprises a generally stem-shaped portion having a top portion that is fitted with coupler means, and this makes it possible, for a screw-type object, to suspend said screw by its body at a height close to the screw head so that the screw is held in reliable manner on the support element, while enabling the operator to see the length of the screw body.

Specifically, in the embodiment shown in FIG. 3, the valve 25 is positioned at the top portion of the stem so that the object that passes through the valve may extend into the space left free between the valve and the bottom portion of the stem. Thus, the length of the object remains visible and the object may be held correctly.

For an object formed of a plurality of hinged-together portions, holding the object suspended also makes it possible to hold said object at said hinge so as to secure it. This is the situation shown in FIG. 3 for which the object suspended through the valve is a "tulip" screw 5' having a head 50' that is hinged to the body via a ball joint. Said screw may be engaged in the orifice of the valve until its head comes into abutment against the edge of the orifice, and this makes it possible to wedge the screw securely, without any risk of the body of the screw moving relative to its head.

In the embodiment shown in the figures, said elements 2, 3, 4 of the package are interfitted, with partial overlap, merely by friction, e.g. by elastic clamping or pressure. Such interfitting, with partial overlap, merely by friction makes it possible to separate said elements by one or both of the operators pulling on one element of the package in natural manner. It is also possible to envisage interfitting, with partial overlap, by clipping.

In a variant, interfitting, with partial overlap, could be achieved by screw-fastening. For screw-fastening, the thread and the tapping formed on the elements to be interfitted are configured in such a manner as to enable said elements to be screw-fastened together only once. In particular, provision may be made for the thread and/or the tapping to deform while screwing on and off, so that the two elements cannot be screwed back together again.

Preferably, the chambers 7 and 8 are impermeable, at least to bacteria. Provision may also be made for them to be impermeable to any fluid. In a variant, provision may be made for one and/or the other of the chambers, and preferably at least the presentation chamber 7 for presenting the object, to be permeable only to gas so as to enable the chamber(s) to be sterilized with gas.

Thus, in a particular embodiment of the invention, provision may be made for at least a portion of the wall of the stopper 3 that defines a portion of the presentation chamber 7 for presenting the object 5 to be formed of material that is permeable to gas but impermeable to bacteria, so as to enable the presentation chamber and the object, e.g. a medical component to be sterilized with gas, e.g. with ethylene oxide or steam. Such a design of the package makes it possible to sterilize the chamber(s) other than by using radiation.

Provision may thus be made for the stopper to be closed, at its end remote from the end that covers the support element in part, by a membrane that is adapted to sterilization by means of a gas.

Advantageously, said object 5 is coupled to the support element 2 in such a manner that its grip end 50 is free and points away from the grip portion 20 of the support element 2 so that the grip zone faces the instrument for gripping the object, and this makes it possible to grip the object easily and rapidly.

The support element 2 and/or the stopper 3 and/or the cover 4 present(s) a portion, preferably formed by a membrane, that is impermeable to bacteria but permeable to gas so as to enable said first chamber 7 and/or said second chamber 8 to be sterilized with gas.

The method of unpackaging an object contained in a package as described above is described below by means of FIGS. 1A, 1B, and 1C in the context of passing a medical component to a "clean" operator, specifically the surgeon in the operating block, via two other operators who are "dirty", i.e. working in a potentially-contaminated environment.

The first operator takes hold of the complete package containing the medical component 5 via the free end 40 of the cover 4 by means of a "dirty" hand MS1. Said first operator thus offers the package to the second operator who takes hold of it via the free end 30 of the stopper by means of a hand MS2 that is also "dirty". With each of the operators holding a respective end of the package in a respective hand, at least one of the two pulls on the package so that the cover is separated from the stopper, while the stopper to which the support element of the medical component is coupled remains in the hand MS2 of the second operator. The distance between the ends 30 and 40 of the package makes it possible to reduce the risk of the support element being contaminated when the chamber 8 is opened by separating the cover and the stopper. As mentioned above, the first operator and the second operator may be the same person.

The grip portion of the support element uncovered in this way remains clean and may be presented to the third operator, namely the surgeon, who uses a "clean" hand MP1 to take hold of said clean end of the support element that is remote from the end 30 of the stopper held by the hand MS2 of the second operator.

At least one of the second and third operators pulls on the sub-assembly formed of the support element and of the stopper so that the presentation chamber 7 for presenting the object opens by means of said support element 2 held by the hand MP1 of the third operator separating from the stopper 3 that remains in the hand MS2 of the second operator.

The third operator can then use the hand MP1 that is holding said support element to deactivate the coupler means without letting go of said support element, and can use the other hand MP2, a "clean hand, to take hold of the object via its free end 50 by means of an instrument 6 in order to implant said object in the body of the patient.

In the embodiment shown in the figures, the support element defines an open cavity housing the object 5, which cavity is to be closed by the stopper 3.

In a variant embodiment that is not shown in the figures, said support element alone defines said first chamber containing said object. To this end, said support element is formed of at least two parts that can be coupled and uncoupled relative to each other, preferably by interfitting with partial overlap, so as to form said first chamber containing said object. In other words, one of the parts of said support element is for closing the open cavity formed by the other part.

In this variant, said stopper is formed by a hollow body having a base portion that includes coupler means for coupling to the support element. Advantageously, the coupler means are configured in such a manner as to make it possible to couple the object to the part of the support element that forms the grip portion of said support element, i.e. the part of the support element that is not directly coupled to the stopper. The stopper and the support element are interfitted by force-fitting an end portion of the support element in a corresponding hollow portion of the stopper. To this end, the hollow portion of the stopper presents lugs that are to be flattened by the support element while said support element is being force-fitted in the stopper. Said lugs are distributed over the inner peripheral face of said stopper around the axis of the stopper.

In such a variant embodiment of the support element, the method described above may be adapted as follows. After the support element 2, held by a clean person, has been separated from the stopper 3, held by a person who might be contaminated, provision may be made for the support element 2 that closes the object 5 to be put in a standby zone, while said object 5 is waiting to be used. Then, said clean person, or another clean person, may open the first chamber 7 defined by said support element 2 by separating the two parts that form said support element, e.g. by unscrewing them, in order to take hold of said medical component.

Thus, the medical component has been neither touched nor let go of during its unpackaging. Furthermore, the chamber containing the medical component is opened only in a clean zone.

As a result of the cover that defines a protective chamber for protecting the grip portion 20 of the support element 2, the clean person touches a clean portion of the package. Specifically, the dirty portions of the package, namely the stopper 3 and the cover 4, remain in the hands of the dirty person. Thus, the hand of the person who takes hold of the support element remains clean.

Preferably, the chambers 7 and 8 are impermeable, at least to bacteria. Provision may also be made for them to be impermeable to any fluid. In a variant, provision may be made for one and/or the other of the chambers, and preferably at least the presentation chamber 7 for presenting the object, to be permeable only to gas so as to enable the chamber(s) to be sterilized with gas.

Thus, in a particular embodiment of the invention, provision may be made for at least a portion of the wall of the stopper 3 that defines a portion of the presentation chamber 7 for presenting the object 5 to be formed of material that is permeable to gas but impermeable to bacteria, so as to enable the presentation chamber and the object, e.g. a medical component to be sterilized with gas, e.g. with ethylene oxide or steam. Such a design of the package makes it possible to sterilize the chamber(s) other than by using radiation.

In particular, provision may thus be made for the stopper to be closed, at its end remote from the end that covers the support element in part, by a membrane that is adapted to sterilization by means of gas.

What is claimed is:

1. A package for an object, the package comprising:
   a support element comprising:
   a coupler configured to hold the object captive in a given orientation of the object, and release the object by pivoting the object, wherein the support element alone defines a first chamber containing the object, the support element further comprises at least two parts that can be coupled and uncoupled relative to each other by inter-fitting with partial overlap, so as to form the first chamber containing the object;
   a first hollow protective element that is a stopper, wherein the stopper is coupled to the support element of the object by inter-fitting with partial overlap such that the support element presents a grip portion that projects from the stopper; and
   a second hollow protective element that is a cover, wherein the cover is coupled to the stopper by inter-fitting with partial overlap so as to cooperate with the stopper to define a second chamber inside which the grip portion of the support element extends, and while the cover is coupled to the stopper, a grip portion of the stopper projects from the cover.

2. The package of claim 1, wherein the coupler comprises a housing in which the object is held by resilient clamping or snap-fastening.

3. The package of claim 1, wherein the support element and the coupler are configured to hold the object so that the length of the object is able to be seen while the object is coupled to the support element.

4. The package of claim 3, wherein the support element further comprises a stem-shaped portion having a top portion that is fitted with the coupler which suspends the object on the support element.

5. The package of claim 1, wherein the support element and the protective elements of the package are inter-fitted, with partial overlap, by friction and/or by screw-fastening.

6. The package of claim 1, wherein at least one of the stopper and the cover presents at least one predefined location to position at least one finger of a person.

7. The package of claim 1, wherein at least one of the support element, the stopper, and the cover presents a portion that is impermeable to bacteria but permeable to gas so as to enable at least one of the first chamber and the second chamber to be sterilized with gas.

8. The package of claim 1, wherein a first part of the supporting element forms an open cavity that is closed by a second part of the support element.

9. The package of claim 8, wherein the stopper comprises a hollow body having a base portion that couples to the first part of the support element.

10. The package of claim 9, wherein the stopper and the first part of the support element are inter-fitted by force-fitting an end portion of the first part of the support element into the base portion of the stopper.

11. The package of claim 1, wherein the at least two parts of the support element are inter-fitted by screw fastening.

12. A method of unpackaging the object contained in the package of claim 1, comprising:
   separating, by a first person, the cover of the package from the stopper of the package to uncover the support element of the package;
   taking hold, by a second person distinct from the first person, of the support element of the package;
   separating the support element from the stopper while the stopper is being held by the first person, the object being captive of the support element in a given orientation; and
   releasing the object from the support element by pivoting the object.

13. The method of unpackaging the object according to claim 12, further comprising:
   putting the support element that closes the object on standby in a standby zone, while the object is waiting to be used; and
   opening the first chamber defined by the support element in order to remove the object.

14. An assembly comprising:
   the object that is a sterilized medical component; and
   the package according to claim 1, the package containing the object coupled to the support element, the object presenting an end configured to be gripped by an instrument, wherein the object is coupled to the support element such that the grip end is free and points away from the grip portion of the support element.

* * * * *